(12) United States Patent
Fischesser et al.

(10) Patent No.: US 7,495,101 B2
(45) Date of Patent: Feb. 24, 2009

(54) MANUFACTURE OF VITAMIN $B_6$

(75) Inventors: Jocelyn Fischesser, Wittenheim (FR);
Helmut Fritsch, Lörrach (DE); Andrew George Gum, Rixheim (FR); Reinhard Karge, Staufen (DE); Ralf Keuper, Lörrach (DE)

(73) Assignee: DSM IP Assets B.V., Heerlen (NL)

( * ) Notice: Subject to any disclaimer, the term of this patent is extended or adjusted under 35 U.S.C. 154(b) by 250 days.

(21) Appl. No.: 10/579,836

(22) PCT Filed: Nov. 9, 2004

(86) PCT No.: PCT/EP2004/012655

§ 371 (c)(1), (2), (4) Date: Jun. 8, 2006

(87) PCT Pub. No.: WO2005/049618

PCT Pub. Date: Jun. 2, 2005

(65) Prior Publication Data

US 2007/0072254 A1       Mar. 29, 2007

(30) Foreign Application Priority Data

Nov. 19, 2003   (DE) ................................ 103 53 999

(51) Int. Cl.
*C07D 471/02* (2006.01)
*C07D 491/02* (2006.01)
*C07D 498/02* (2006.01)

(52) U.S. Cl. ...................................... 546/115; 546/116

(58) Field of Classification Search ................. 546/115, 546/116
See application file for complete search history.

(56) References Cited

U.S. PATENT DOCUMENTS 3,250,778 A * 5/1966 Kimel et al. ................... 546/15
3,296,275 A   1/1967 Schaeren
3,822,274 A   7/1974 Harris et al.

FOREIGN PATENT DOCUMENTS

WO   WO 2004/058775   7/2004

OTHER PUBLICATIONS

International Search Report.

* cited by examiner

*Primary Examiner*—Janet L Andres
*Assistant Examiner*—Niloofar Rahmani
(74) *Attorney, Agent, or Firm*—Nixon & Vanderhye P.C.

(57) ABSTRACT

A process for manufacturing a 3-unsubstituted, 3-monosubstituted or 3,3-disubstituted 9-acyloxy-1,5-dihydro-8-methylpyrido[3,4-e][1,3]dioxepin (I) and optionally for manufacturing pyridoxine involves performing an addition reaction between a 4-methyl-5-alkoxy-oxazole (II) and a 2-unsubstituted, 2-monosubstituted or 2,2-disubstituted 4,7-dihydro-(1,3)-dioxepin (III) in the substantial absence of a solvent and a catalyst to give a product mixture consisting essentially of the appropriate Diels-Alder adduct (IV) in a major proportion and the appropriate 3-unsubstituted, 3-monosubstituted or 3,3-disubstituted 1,5-dihydro-8-methylpyrido[3,4-e][1,3]dioxepin 9-ol (V) in a minor proportion, removal of a substantial proportion of the unreacted oxazole and dioxapin starting materials from the product mixture by distillation under reduced pressure, addition of a substantially anhydrous organic acid to said product mixture and rearrangement of the Diels-Alder adduct IV to further V in the presence of said substantially anhydrous organic acid with removal of the generated alkanol by distillation under reduced pressure, and acylation of the resultingly enriched quantity of V with an added carboxylic acid anhydride to produce the desired I, and optionally converting this so-manufactured acylation product I to pyridoxine by acid hydrolysis for achieving deprotection and deacylatiom. Pyridoxine is a well known form of vitamin $B_6$ with well established utility.

21 Claims, No Drawings

MANUFACTURE OF VITAMIN B$_6$

This application is the US national phase of international application PCT/EP20041/012655 filed 9 Nov. 2004 which designated the U.S. and claims benefit of DE 103 53 999.9, dated 19 Nov. 2003, the entire content of which is hereby incorporated by reference.

The present invention concerns certain process steps in the multistep manufacture of vitamin B$_6$ (pyridoxine).

It is known from the patent and scientific literature that the chemical synthesis of vitamin B$_6$ generally involves the reaction of a 4-methyl-5-alkoxy-oxazole or of 4-methyl-5-cyano-oxazole with a 2-unsubstituted, 2-monosubstituted or 2,2-disubstituted 4,7-dihydro-(1,3)-dioxepin (the latter compound being in effect a protected 2-butene-1,4-diol), i.e. by a Diels-Alder addition reaction, to form the corresponding Diels-Alder adduct, rearrangement of said adduct under acidic conditions to form 1,5-dihydro-8-methylpyrido[3,4-e][1,3]dioxepin-9-ol or its corresponding 3-monosubstituted or 3,3-disubstituted derivative, and conversion of the last-mentioned compound (in effect a "deprotection" of two adjacent linked hydroxymethyl substituents on the 3- and 4-positions of 5-hydroxy-6-methyl-pyridine) by acid hydrolysis to produce the desired vitamin B$_6$.

This route is described in U.S. Pat. No. 3,250,778, for example, albeit with little emphasis on the formation of the Diels-Alder adduct and its rearrangement to the pyrido[3,4-e][1,3]dioxepinol intermediate: it is merely stated that the intermediate Diels-Alder adduct collapses under the conditions of the reaction between the oxazole and dihydrodioxepin starting materials to form the aforementioned intermediate, i.e. the precursor for vitamin B$_6$. Indeed, a preferred embodiment even involves the direct production of vitamin B$_6$ or a related end product from the starting materials without isolation of the pyrido[3,4-e] [1,3]dioxepinol intermediate using acidic conditions which are also suitable for the final hydrolysis step. A further embodiment described in this U.S. patent specification involves the reaction of the oxazole and dioxepin starting materials in the presence of an alkanoylating agent, e.g. a lower alkanoyl halide or lower alkanoic acid anhydride, to obtain the pyrido[3,4-e] [1,3]dioxepinol intermediate in which the 9-hydroxyl substituent is esterified, the esterified hydroxyl group then being freed of its alkanoyl moiety by the subsequent acid hydrolysis.

The reaction to produce the isolable non-esterified pyrido[3,4-e] [1,3]dioxepinol intermediate or its esterified derivative can be acid catalyzed, e.g. with acetic acid; however in U.S. Pat. No. 3,250,778 it is also stated that the use of such (acid) agents is not preferred in view of the acid sensitivity of the oxazole starting material. Moreover, there is no suggestion in this USP of involving the use of an acid after the acid-free Diels-Alder reaction of the oxazole and dihydrodioxepin starting materials and before any desired esterification of the produced pyrido[3,4-e] [1,3]dioxepinol intermediate with an alkanoylating agent.

U.S. Pat. No. 3,296,275 also describes a process for manufacturing vitamin B$_6$ and related pyridine derivatives starting from a 4-alkyl-5-alkoxy-oxazole and a 2-unsubstituted, 2-monosubstituted or 2,2-disubstituted 4,7-dihydro-(1,3)-dioxepin by a Diels-Alder addition reaction to form an adduct, which is then isolated and in a separate step rearranged in a weakly acid medium to form the desired pyridine derivative, being actually a 3-unsubstituted, 3-monosubstituted or 3,3-disubstituted 1,5-dihydro-8-alkylpyrido[3,4-e] [1,3]dioxepin-9-ol; the product can be hydrolysed to the corresponding 5-hydroxy-6-alkyl-3,4-dihydroxymethyl-pyridine, e.g. vitamin B$_6$ (pyridoxine; alkyl=methyl), by known means, particularly in an acid medium of higher acidity than that of the medium in which the prior rearrangement of the Diels-Alder adduct is effected. The aforementioned rearrangement is said to be effected using for example hydrochloric, sulphuric, tartaric or oxalic acid, or even pyridoxine hydrochloride, as the acidic agent, preferably in aqueous lower alcohol solution, to afford a weakly acid medium with a pH of about 2.3 to about 3.5. In this USP, however, there is no suggestion of esterifying the rearrangement product.

Accordingly to the process which is the subject of a further U.S. patent specification U.S. Pat. No. 3,822,274, the oxazole and "2-butene" (e.g. 2-monosubstituted or 2,2-disubstituted 4,7-dihydro-1,2-dioxepin) derivatives are reacted in the presence of an acid binding agent, i.e. an inorganic or organic base, an epoxide, a molecular sieve or calcium carbide, to promote an increased yield of the pertinent Diels-Alder adduct. After the completion of the adduct formation the adduct is isolated and converted to a substituted pyridine, being a pyridoxine precursor or directly formed pyridoxine. In those Examples (4 and 5) involving the reaction of 4-methyl-5-ethoxy-oxazole with 4,7-dihydro-2-isopropyl-(1,3)-dioxepin or the corresponding 2,2-dimethyl substituted dihydrodioxepin, calcium oxide is used as the acid binding agent and the so produced Diels-Alder adduct is isolated by removal of unreacted starting materials and dissolved in glacial acetic acid containing added water, the resulting solution then being allowed to stand for several hours and subsequently heated and concentrated (and filtered) to afford pyridoxine. Dissolution of the product in hydrochloric acid and heating/crystallization yields the hydrochloride salt. An esterification step is not foreseen.

Indian Patent Specification 175,617 describes the Diels-Alder addition reaction of 4-methyl-5-alkoxy-oxazole with a 2-substituted 4,7-dihydro-(1,3)-dioxepin in a sealed tube, in the absence of both solvent and catalyst, to form the corresponding Diels-Alder adduct whereby microwave irradiation is used as the heating means, creating a reaction temperature which is less than 120° C. Thereafter, the excess dioxepin reactant is distilled off. The produced Diels-Alder adduct can then be transformed directly into vitamin B$_6$ by reaction with hydrochloric acid, particularly according to the method described in J. Org. Chem., 27, 2705 (1962), this being exemplified in Example 3 of the patent specification. In this specification, too, there is no suggestion of forming a rearrangement product from the Diels-Alder adduct and esterifying it.

The previously known processes for the manufacture of vitamin B$_6$, e.g. those described in the above-reviewed patent specifications insofar as the process steps from the Diels-Alder reaction to the esterification process (if the latter is employed) are involved, feature certain disadvantages, such as inadequate yields and purities of intermediate products, difficulties in respect of recycling unreacted starting materials as a result of the use of certain solvents and/or catalysts in particular reaction steps, and the corrosive action of strong acids employed in such reaction steps.

The object of the present invention is to provide a process for the manufacture of a hydroxyl-protected 5-acyloxy-3,4-dihydroxymethyl-6-methyl-pyridine, being a vitamin B$_6$ precursor, which does not have the above-indicated disadvantages, at least, of the previously known processes, and optionally for the manufacture of pyridoxine.

Accordingly, the present invention provides a process for manufacturing a 3-unsubstituted, 3-monosubstituted or 3,3-disubstituted 9-acyloxy-1,5-dihydro-8-methylpyrido[3,4-e][1,3]dioxepin of the general formula

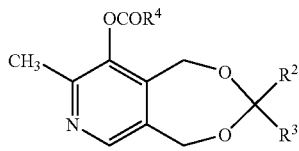

wherein each of $R^2$ and $R^3$, independently, signifies hydrogen, $C_{1-4}$-alkyl, $C^{2-4}$-alkenyl, phenyl-$C_{1-4}$-alkyl or phenyl, or $R^2$ and $R^3$ together with the carbon atom to which they are attached signify $C_4$- to $C_6$-cycloalkylidene, and $R^4$ signifies $C_{1-4}$-alkyl or $C_{1-4}$-haloalkyl, and optionally for manufacturing pyridoxine, characterized by performing an addition reaction between a 4-methyl-5-alkoxy-oxazole of the general formula

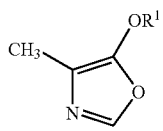

wherein $R^1$ signifies $C_{1-4}$-alkyl, and a 2-unsubstituted, 2-monosubstituted or 2,2-disubstituted 4,7-dihydro-(1,3)-dioxepin of the general formula

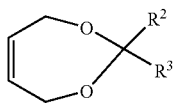

wherein $R^2$ and $R^3$ have the above-mentioned significances, in the substantial absence of a solvent and a catalyst to give a product mixture consisting essentially of the appropriate Diels-Alder adduct (5-unsubstituted, 5-monosubstituted or 5,5-disubstituted 1-alkoxy-11-methyl-4,6,12-trioxa-10-azatricyclo[7.2.1.0$^{2,8}$]dodec-10-ene) of the general formula

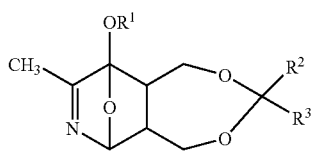

wherein $R^1$, $R^2$ and $R^3$ have the above-mentioned significances, in a major proportion and the appropriate 3-unsubstituted, 3-monosubstituted or 3,3-disubstituted 1,5-dihydro-8-methylpyrido[3,4-e] [1,3]dioxepin-9-ol of the general formula

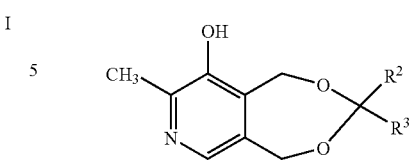

wherein $R^2$ and $R^3$ have the above-mentioned significances, in a minor proportion, removal of a substantial proportion of the unreacted starting materials of formulae II and III from the product mixture by distillation under reduced pressure, addition of a substantially anhydrous organic acid to said product mixture and rearrangement of the Diels-Alder adduct of the formula IV present therein to further 3-unsubstituted, 3-monosubstituted or 3,3-disubstituted 1,5-dihydro-8-methylpyrido[3,4-e] [1,3]dioxepin-9-ol of the formula V in the presence of said substantially anhydrous organic acid with removal of the generated alkanol $R^1OH$ by distillation under reduced pressure, and acylation of the resultingly enriched quantity of the methylpyrido[3,4-e] [1,3]dioxepin-9-ol of the formula V with an added carboxylic acid anhydride of the general formula $$(R^4CO)_2O \qquad VI$$

wherein $R^4$ has the above-mentioned significance, to produce the desired 3-unsubstituted, 3-monosubstituted or 3,3-disubstituted 9-acyloxy-1,5-dihydro-8-methylpyrido[3,4-e] [1,3]dioxepin of the formula I, and optionally converting this so-manufactured acylation product of the formula I to pyridoxine by acid hydrolysis for achieving deprotection and deacylation.

In the above definitions of the starting materials of the formulae II and III, and as also applicable to the pertinent significances featured by the appropriate intermediate products and the final product of the process according to the present invention, any alkyl, alkenyl or $C_{1-4}$-haloalkyl group containing three or more carbon atoms can be straight chain or branched. Thus $C_{1-4}$-alkyl and $C_{2-4}$-alkenyl may be, for example, methyl, ethyl, n-propyl, isopropyl, n-butyl or isobutyl; and vinyl, 1- or 2-propenyl or 2-methyl-2-propenyl, respectively. The $C_{1-4}$-alkyl part of phenyl-$C_{1-4}$-alkyl may similarly be straight chain or branched, indeed from $C_2$ [as —CH(CH$_3$)—]. Where $R^2$ and $R^3$ together with the carbon atom to which they are attached signify $C_4$-$C_6$-cycloalkylidene, then the pertinent cycloalkane moiety thereof is cyclobutane, cyclopentane or cyclohexane, respectively. In this case, and as a further explanation, $R^2$ and $R^3$ themselves together form tri-, tetra- or pentamethylene, respectively. The or each halogen substituent of $C_{1-4}$-haloalkyl is fluorine, chlorine or bromine, preferably fluorine or chlorine, most preferably fluorine. There may be one or more (same or different) halogen substituents, but the haloalkyl group preferably features a single (type of) halogen substituent. Preferably $C_{1-4}$-haloalkyl is trifluoromethyl or trichloromethyl, most preferably trifluoromethyl.

The preferred starting materials of formulae II and III in the process of the present invention are 5-ethoxy-4-methyl-oxazole (formula II wherein $R^1$ signifies ethyl) and 2-isopropyl-4,7-dihydro-(1,3)-dioxepin (formula III wherein $R^2$ signifies hydrogen and $R^3$ signifies isopropyl), respectively.

The first step of the process of the present invention, i.e. the (Diels-Alder) addition reaction between the compounds of the formulae II and III, is effected in the substantial absence of a solvent, which means that effectively no solvent is employed for the pertinent reaction. Indeed it has been found that the reaction proceeds without the need for a solvent, and so no solvent is deliberately added to or otherwise included in the reaction mixture. Furthermore, and in contrast to certain known processes for reacting these compounds, no catalyst is employed either. In this regard it is noted that the prior art processes can involve acid catalysis, e.g. as described in U.S. Pat. No. 3,250,778, or basic catalysis, e.g. as described in U.S. Pat. No. 3,822,274, or catalysis with another kind of "acid binding agent", as further described in the latter USP. Accordingly, this first process step is initiated by bringing the two starting materials in the substantial absence of any other materials into contact for reaction at a suitable temperature.

The first process step is conveniently effected at temperatures from about 130° C. to about 170° C., preferably from about 145° C. to about 160° C., and most preferably at a temperature of about 155° C. Under such temperature conditions the production of the Diels-Alder adduct of formula IV is promoted to a much greater extent than that of the methylpyrido[3,4-e] [1,3]dioxepin-9-ol of formula V; indeed, in this process step a maximum possible ratio of the adduct to the methylpyrido[3,4-e] [1,3]dioxepin-9-ol is desired. Moreover, it is found that the loss of the 4-methyl-5-alkoxy-oxazole as an unreacted constituent of the reaction mixture is minimized, i.e. that it is consumed in the reaction to a large extent. The aforementioned product ratio (IV:V) achieved is usually in the range from about 2:1 to about 10:1, e.g. is about 7:1 in favour of the Diels-Alder adduct of formula IV.

Furthermore, the molar ratio of the dihydrodioxepin of the formula III to the 4-methyl-5-alkoxy-oxazole of the formula II in the reaction mixture is conveniently from about 0.5:1 to about 5:1, preferably from about 1:1 to about 2:1, and most preferably about 1.3:1. In general it is found that the preferred excess of the dihydrodioxepin over the 4-methyl-5-alkoxy-oxazole promotes the homogeneity of the reaction mixture and that the required extent of this excess is reduced as the reaction temperature is decreased, i.e. that the larger the excess molar amount of the dihydrodioxepin over the molar amount of the 4-methyl-5-alkoxy-oxazole, the higher the reaction temperature should be, and the smaller this excess, the lower the reaction temperature should be, for a favourable outcome of the reaction in respect of the space-time yield.

As regards the duration for performing the reaction it is generally convenient, taking account of the known thermal sensitivity of 4-methyl-5-alkoxy-oxazoles and for the desired promotion of a maximum yield of the Diels-Alder adduct of formula IV, to employ shorter reaction times at higher temperature and higher reaction times at lower temperatures. In these circumstances the reaction duration is conveniently from about 2 to about 8 hours, preferably from about 3 to about 5 hours, and most preferably about 4 hours.

In general the reaction mixture is conveniently agitated throughout the reaction duration, preferably by constant stirring, in a reaction vessel/reactor. If desired, the two reactants of formulae II and III can be mixed, and optionally also preheated at least to some extent up to the reaction temperature, before being introduced into the reaction vessel/reactor in which the Diels Alder reaction actually takes place. Moreover, the process is conveniently carried out under an inert gas atmosphere, preferably gaseous nitrogen or argon, more preferably the former.

The second process step, i.e. the removal of a substantial proportion, i.e. as much as possible, of the unreacted starting materials from the product mixture obtained after the first step, is effected by distillation under reduced pressure, conveniently at a pressure in the range from about 10 mbar (1 kPa) to about 100 mbar (10 kPa), preferably from about 20 mbar (2 kPa) to about 50 mbar (5 kPa), most preferably from about 35 mbar (3.5 kPa) to about 45 mbar (4.5 kPa).

During the distillation the product mixture remains homogeneously fluid at the elevated temperature, especially when said temperature is above about 80° C. After completion of the distillation it is advantageous to maintain the homogeneous fluidity of the concentrated product mixture by appropriate continued heating prior to the next (third) process step.

The third process step involves the addition of a substantially anhydrous organic acid to the product mixture of a major proportion of the Diels-Alder adduct of formula IV and a minor proportion of the methylpyrido[3,4-e] [1,3]dioxepinol of formula V, and the ensuing rearrangement of the Diels-Alder adduct, catalyzed by the added acid, to further methylpyrido[3,4-e] [1,3]dioxepinol, with removal of generated alkanol $R^1OH$ by reduced pressure distillation. As the substantially anhydrous organic acid there may be used in general an organic (carboxylic) acid with a pKa value of up to about 5, and in particular a $C_{2-5}$-alkanoic acid, i.e. acetic, propionic, butyric or valeric acid (pKa value in the region of about 4 to 5), or a corresponding mono- or multihalogenated $C_{2-5}$-alkanoic acid (trifluoro- and trichloroacetic acid, for example, have pKa values of about −0.25 and about 0.65, respectively), of which acetic acid is preferred. The expression "substantially anhydrous" in this context means that the organic acid is non-aqueous (e.g. is glacial acetic acid as opposed to aqueous acetic acid), containing as little water as possible, and that no water is added either to the acid or to the process step in which the acid is used. It is often unavoidable, however, that trace amounts of water may be present, e.g. in the commercially obtained acid (e.g. depending on the source glacial acetic acid may contain up to about 0.1% by weight of water) or otherwise in the vessel/reactor in which the third process step is carried out; accordingly, such an acid, although not being completely anhydrous, is embraced by the expression "substantially anhydrous organic acid".

The amount of acid added in this process step is based upon the estimated or determined amount of the produced Diels-Alder adduct in the product mixture, or alternatively of consumed 5-ethoxy-4-methyl-oxazole from the first reaction step, and is suitably from about 0.01 equivalents (a catalytic amount) to about 2.0 equivalents per equivalent of said adduct, preferably from about 1 to about 1.5 equivalents. With a catalytic amount of acid, the rearrangement of the Diels-Alder adduct will occur, but undesirably slowly. Moreover, the addition of the acid is suitably effected to the product mixture at a temperature from about 50° C. to about 115° C., preferably when the temperature of the mixture is from about 70° C. to about 90° C. At such temperatures the product mixture containing the Diels-Alder adduct is generally, and desirably, in the fluid state, and remains so after completion of the acid addition.

The rearrangement reaction can then be effected suitably by stirring the acidified mixture under the aforementioned temperature conditions for sufficient time to achieve the desired complete or virtually complete rearrangement of the Diels-Alder adduct to the desired further quantity of methylpyrido[3,4-e] [1,3]dioxepinol of the formula V. In general the rearrangement is faster on using higher relative amounts of the anhydrous organic acid, and the rearrangement can usually be completed within about two hours. During the rearrangement any oxazole of the formula II or dihydrodioxepin of the formula III which may still have remained unreacted from the first process step is generally fully destroyed by the acid used in this third process step.

As indicated above, the rearrangement is effected at a reduced pressure to enable the generated alcohol R$^1$OH to be removed from the reaction mixture by distillation. Said reduced pressure is suitably from about 300 mbar (30 kPa) to about 700 mbar (70 kPa). At the distillation temperature, when the reduced pressure drops below about 300 mbar, an azeotropic mixture of the generated alcohol R$^1$OH and the employed substantially anhydrous organic acid tends to form, especially when using the preferred acid acetic acid and the alcohol is ethanol (R$^1$ is ethyl).

At the termination of this third process step under the aforementioned reaction conditions, including the reduced pressure, the alcohol R$^1$OH is completely, or virtually completely removed. It is important that as little alcohol as possible finally remains so as to avoid in the final (fourth) process step, i.e. the acylation with the carboxylic acid anhydride of the formula VI, the undesired formation of esters by the reaction of the alcohol with the acid anhydride, e.g. ethyl acetate from ethanol and acetic anhydride.

The final step of the process of the present invention, in so far as the manufacture of the acylation product of the formula I is concerned, involves the acylation of the methylpyrido[3,4-e][1,3]dioxepinol of the formula V with a carboxylic acid anhydride. Said acid anhydride is conveniently the anhydride corresponding to the substantially anhydrous acid used in the previous process step, e.g. acetic anhydride or trifluoroacetic anhydride where acetic acid or trifluoroacetic acid, respectively, was used previously. As acetic acid is the preferred substantially anhydrous acid in the previous, rearrangement step, so is acetic anhydride the preferred acylating agent in the present process step, giving rise to a product of the formula I wherein R$^4$ signifies methyl.

In general, the amount of carboxylic acid anhydride employed for the acylation is an excess amount based on the estimated or determined amount of the methylpyrido[3,4-e][1,3]dioxepinol to be acylated, and said amount is conveniently from about 1.05 to about 2 equivalents per equivalent of the aforementioned dioxepinol, preferably from about 1.1 to about 1.5 equivalents. Conveniently, the carboxylic acid anhydride is added to the mixture in the vessel (reactor) used in the previous process step, thus avoiding a removal and transfer prior to the acylation.

The temperatures at which the acylation is conveniently effected are from about 50° C. to about 115° C., preferably from about 70° C. to about 90° C. Thus they are in the same region as for the previous, rearrangement step, indeed inter alia for the same purpose of maintaining the reaction mixture in the fluid state throughout the reaction, thus enabling it to be agitated, preferably by stirring, during the acylation.

The acylation is continued conveniently as long as necessary for achieving a maximum degree of acylation, and is usually complete within about one hour.

The resulting acylated product, i.e. the desired 3-unsubstituted, 3-monosubstituted or 3,3-disubstituted 9-acyloxy-1,5-dihydro-8-methylpyrido[3,4-e][1,3]dioxepin of the formula I, is suitably continuously isolated from the mixture during the acylation by distillation under reduced pressure. Said reduced pressure is conveniently from about 0.01 bar (1 kPa) to about 0.1 bar (10 kPa). Under these same pressure conditions the carboxylic acid R$^4$COOH formed as a byproduct of the acylation can also be removed by distillation under reduced pressure, and if desired recycled, e.g. back to the previous step of the process to serve as or augment the amount of the substantially anhydrous acid. The desired product is generally obtained in good purity and yield, and can be stored if desired before converted (by acid hydrolysis to achieve deprotection and deacylation) at will to vitamin B$_6$ (pyridoxine), e.g. by procedures well known in the prior art.

This conversion of the acylation product of the formula I to pyridoxine is the optional final step of the process of the present invention, and is realizable by procedures well known in the prior art, such as described in the previously reviewed U.S. Pat. No. 3,250,778 (column 4, lines 3-10, and Example 23). Depending on the type of acid involved in the acid hydrolysis the pyridoxine may be produced and isolable in the form of the appropriate acid salt, e.g. the hydrochloride when hydrochloric acid is used as the acid.

In each step of the whole multistep process in accordance with the invention the progress of the pertinent reaction can be monitored by analytical methods conventionally employed in organic chemistry, e.g. by periodically removing small samples of the reaction mixture and analyzing their content using such analytic methods as gas chromatography, liquid chromatography, ultraviolet spectroscopy and/or infrared spectroscopy.

The whole multistep process in accordance with the invention can be carried out batchwise at each stage or continuously for two or more steps, preferably continuously, and in general operationally in a very simple manner. As an example of the continuous methodology there may be mentioned the performance of the first process step in a flow-through reactor which is connected to a continuous distillation unit in which the second process step, i.e. the distillative removal of a substantial proportion of the unreacted starting materials of formula II and III from the product mixture under reduced pressure, is effected; more specifically, the reactor into which the starting materials are introduced for the Diels-Alder addition reaction is a cascade reactor, and the connected continuous distillation unit is a falling film or thin film evaporator. Furthermore, the third and fourth process steps can be performed consecutively in the same reaction vessel/reactor.

The starting materials of the formulae II and III used in the process of the present invention are in some cases known compounds, or, where not previously known, can be produced by analogous methods to the pertinent known ones. In respect of the 2-unsubstituted, 2-monosubstituted or 2,2-disubstituted 4,7-dihydro-(1,3)-dioxepins of the formula III these may be considered as being in each case a hydroxyl protected 1,4-dihydroxy-2-butene, and methods for producing them by appropriately "protecting" said dihydroxybutene are for example described and exemplified in U.S. Pat. No. 3,250,778.

One advantage of the process in accordance with the invention is, in addition to a high overall yield of final product, the avoidance, through the employment of the special reaction conditions, of obtaining too much 3-unsubstituted, 3-monosubstituted or 3,3-disubstituted 1,5-dihydro-8-methylpyrido[3,4-e][1,3]dioxepin-9-ol of the formula V as a product of the first process step (the Diels-Alder reaction). Said product has been found to have the disadvantageous effect of decomposing the one starting material 4-methyl-5-alkoxy-oxazole of the general formula II during the Diels-Alder reaction at higher temperatures than those which are employed in the inventive process for maximizing the proportion of the Diels-Alder adduct obtained at this stage of the process. A further advantage is the avoidance in the subsequent rearrangement step (IV→V) of using a strong acid such as hydrochloric acid which is more corrosive than the substantially anhydrous acid used in the inventive process and which would tend to convert the Diels-Alder adduct directly to pyridoxine which would be so obtained in a significantly less pure state than that obtained via its more easily purifiable acylate; accordingly an undesirable production of excessive byproducts is avoided by the process in accordance with the invention. It follows that since the final acylated product of the inventive process, i.e. the 3-unsubstituted, 3-monosubstituted or 3,3-disubstituted 9-acyloxy-1,5-dihydro-8-methylpyrido[3,4-e] [1,3]dioxepin of the formula I, is more easily purifiable than pyridoxine; the latter product, when obtained from the acylated product by hydrolysis, is itself purer from the outset and requires less purification. Yet another advantage of the process in accordance with the present invention is that the reaction mixtures in each of the main process steps of Diels-Alder reaction, rearrangement and acylation remain homogeneous, thus allowing the employment of inter alia flow-through and cascade reaction systems. As desired, these three main process steps can each be effected batchwise, or two or all three be effected in a single batch reactor or e.g. as a continuous cascade process. Furthermore, recycling of the unreacted starting materials and, for example, of the carboxylic acid byproduct of the final acylation process step to the previous rearrangement step is practicable by the process of the present invention.

The process in accordance with the present invention is illustrated by the following Examples:

EXAMPLE 1

Batch Diels-Alder Reaction of 5-ethoxy-4-methyl-oxazole and 2-isopropyl-4,7-dihydro-(1,3)-dioxepin To a 350 ml reaction flask were added under an argon atmosphere 30.7 g (239 mmol, 1 equivalent) of 5-ethoxy-4-methyl-oxazole (EMO) followed by 45.7 g (310 mmol, 1.3 equivalents) of 2-isopropyl-4,7-dihydro-(1,3)-dioxepin (IPD). The reaction mixture was stirred at 200 rpm and heated at 155° C. (internal temperature) for 4 hours. The Diels-Alder reaction was monitored by gas chromatography (GC), samples being removed from the reactor at 1 hour intervals (samples of 10 μL reaction mixture diluted with 1 ml of ethyl acetate). After 4 hours the reaction mixture was cooled to room temperature. Calibrated GC analysis (w/w %) showed that the reaction mixture contained the desired products, i.e. the Diels-Alder adduct (ADDI) and 1,5-dihydro-3-isopropyl-8-methylpyrido[3,4-e] [1,3]dioxepin-9-ol (PIB) in the relative amounts 18.9 w/w % and 6.7 w/w %, respectively, as well as unreacted EMO (21.4 w/w %) and IPD (42.3%) and the isonitrile by-product ethyl 2-isocyanopropionate (EIPA, 2.5 w/w %). The remaining 11 w/w % of the reaction mixture consisted of unidentifiable substances. The yield of the Diels-Alder adduct based on the amount of EMO used was 31.5%, whereby 53.1% of the EMO was recycled.

EXAMPLE 2

Recycled Batch Diels-Alder Reaction EMO+IPD

Into a 500 ml double-jacketed reactor under an atmosphere of argon were introduced 183.4 g of EMO/IPD distillate (189 ml containing 397 mmol of EMO and 873 mmol of IPD; EMO:IPD 27.5 w/w %:67.7 w/w % according to GC; distillate density 0.97 g/ml). To the EMO/IPD distillate were added 45.2 g of fresh technical grade EMO (44 ml, 353 mmol, EMO quality 99.4 w/w %) and 15.0 g of technical grade IPD (15.5 ml, 102 mmol, IPD quality 96.7 w/w %). The stoichiometry of the reaction mixture, i.e. the molar ratio EMO:IPD, was 1:1.3, and the recycled batches were kept at constant volumes (750 mmol of EMO, 975 mmol of IPD, total reactant volume 250 ml). The reaction mixture was submitted to a reduced pressure of 150 mbar (15 kPa) and stirred at 250 rpm. The mantle temperature was raised to 100° C. over 1.5 hours. At the same time, the partial condensation head (dephlegmator) was also heated to 100° C. The internal temperature of the reactor reached 90-95° C. The reactor was maintained at this temperature, and low boiling by-products, mainly ethanol, were removed during a predistillation over 2 hours and collected in a cold trap at −78° C. The reduced pressure of the system was adjusted to 900 mbar (90 kPa), and the mantle temperature was raised to 159° C. over 3 hours, at the end of which the internal temperature of the reaction mixture had reached 155° C. This temperature was held for a further 4 hours, during which the low boiling constituents, mainly ethanol, were constantly removed and collected in 2 cold traps connected in series to insure complete trapping of said low boiling constituents. At the end of this Diels-Alder reaction time, the mantle temperature was lowered to 30° C. over 3 hours. The complete reaction process time amounted to 13.5 hours. The brownish crude reaction mixture was then transferred from the bottom of the reactor into a beaker, and the reactor was rinsed with 27.1 g (28 ml, 190 mmol) of additional IPD to ensure complete removal of the Diels-Alder -products. The complete reaction mixture was transferred to a second reactor for the distillation step.

EXAMPLE 3

Distillation of Crude Diels-Alder Reaction Mixture

To a 500 ml double-jacketed reactor under an argon atmosphere was added the crude Diels-Alder reaction mixture obtained as described in Example 2. The flask was rinsed with 17.3 g (17 ml, 122 mmol) of additional IPD to ensure complete transfer of the components. A reduced pressure of 30 mbar (3 kPa) was applied to the system. The mixture was stirred and the mantle temperature was raised to 110° C. over 2 hours, during which the partial condensation head (dephlegmator) was heated to 100° C. The unreacted EMO/IPD was distilled off under reduced pressure as a mixture and collected into a receiver. During the 4 hours distillation time, the mantle temperature was programmed to rise to 130° C. At the end of the distillation, the mantle temperature was lowered to 80° C. over 1 hour, the complete distillation cycle lasting 7 hours. The resulting dark brown, crude product mixture was transferred to a round-bottomed flask. GC analysis showed that ADDI (72.6 w/w %) and PIB (14.5 w/w %) were the major products and that the overall yield based on EMO at the end of the process cycle was 35.0%, whereby 54.4% of the EMO was recycled.

EXAMPLE 4

Diels-Alder Reaction in a Cascade Reactor System

To the bottom of a first reactor (1) in a cascade system consisting of three 1 liter glass, double-jacketed, independently heated reactors equipped with separate thermometer and controllers were added continuously via separate feed lines connected to HPLC pumps EMO and recycled IPD distillate (containing 91.3% IPD and 4.2% EMO). To adjust the stoichiometry, fresh EMO was added. The total amount of reactants added to the cascade system was 562 g (4.4 mol) of EMO and 1256 g (8.8 mol, 2 equivalents) of IPD. The Diels-Alder reaction occurred in reactors 1 and 2 at 150° C. and the product stream was cooled in reactor 3 at 30° C. To remove the low boiling constituents from the mixture during the reaction a condensation bridge at 70° C. as well as two cold traps at −78° C. connected in series to the condensation bridge were used. A counter-stream of nitrogen gas was used to assist in removing the low boiling constituents. The transfer of the reaction solution between reactors occurred by gravity spill-over from the top of the reactor. The Diels-Alder reaction time was 6 hours (after 18 hours equilibration time). The product stream was collected in a catch vessel, where the weight of the crude product was recorded by an independent balance. Unreacted EMO and IPD were removed from the mixture by rotary evaporation under reduced pressure, and a crude product containing ADDI (56.8 w/w % GC) and PIB (22.8 w/w % GC) was isolated. The yield of ADDI based on the EMO at the end of the process cycle was 30.8%, whereby 64.0% of the EMO was recycled.

EXAMPLE 5

Rearrangement of ADDI to PIB

The crude Diels-Alder product mixture weighing 92.4 g (279.3 mmol, containing 225.7 mmol of ADDI, 65.8 w/w % GC, and 53.6 mmol of PIB, 13.0 w/w % GC) was heated in a water bath at 80° C. until the mixture had become fluid, the heating time being approximately 30 minutes. To the stirred reaction mixture (100 rpm) at 80° C. were added dropwise 15 ml of acetic acid (263 mmol, 1.16 equivalents calculated from ADDI) through Metrohm Dosimat over 15 minutes. After the addition of acetic acid, a reduced pressure of 300 mbar (30 kPa) was applied to the reactor and the low boiling products, mainly ethanol, were trapped in a Liebig condenser at −78° C. during the course of the reaction. After the addition of the acid, an exothermic reaction was observed and the internal temperature of the reaction mixture reached about 92° C. The mixture was stirred for 2 hours at 80° C. and monitored by GC (10 mg samples of reaction mixture dissolved in 1 ml of ethyl acetate containing 1% of triethylamine). After 2 hours, no ADDI starting material was observed by GC (less than 0.1 w/w %). PIB was observed by GC as the only major product (60.7 w/w % GC, 273.7 mmol). From the GC analysis, the yield of the rearrangement was 98%. The crude PIB ("rearrangement mixture") was used directly in the next process step described in Example 6 below.

EXAMPLE 6

Acetylation of PIB to 9-acetoxy-1,5-dihydro-3-isopropyl-8-methylpyrido[3,4-e] [1,3]dioxepin 46.44 ml of acetic anhydride (488 mmol, 1.75 equivalents calculated from PIB) were added dropwise over 5 minutes to the crude rearrangement mixture (see Example 5) at 80° C. in the same 250 ml reactor. The reaction mixture was then stirred at 80° C. for 1 hour and monitored by GC (10 mg samples of reaction mixture dissolved in 1 ml of ethyl acetate containing 1% of triethylamine). After 1 hour only traces of PIB starting material were observed by GC (less than 0.5 w/w %) and the reaction mixture was used directly in the following distillation step.

On the same 250 ml reactor used in the rearrangement reaction the reflux condenser was replaced by a distillation head and Vigreux column equipped with an independent heating coil. A Liebig condenser with circulation thermostat and simple fraction collector was connected to the distillation head. With the reaction mixture still at 80° C. (bath temperature 90° C.), the reduced pressure distillation was started at 200 to 20 mbar (20 to 2 kPa) with a membrane pump, and a prefraction containing acetic acid and acetic anhydride was collected. The simple fraction collector was then exchanged for a glass cow adapter for fraction collection. The Liebig condenser as well as the distillation head and Vigreux column were heated to 120° C. Some polyethylene glycol 400 (2 ml) was added to dilute the reaction mixture and to assist in the complete distillation of all the desired product, 9-acetoxy-1, 5-dihydro-3-isopropyl-8-methylpyrido[3,4-e] [1,3]dioxepin (PIB acetate). Isobutyral acetate was first removed under a reduced pressure of about 0.1 to 0.01 mbar (about 10 to 1 Pa) and then the distillation of PIB-acetate was conducted by slowly warming the mixture from 80° C. to 145° C. over several hours. Fractions were collected and analyzed. The desired PIB acetate was collected in 4 main fractions as a viscous, light yellow oil (71.1 g, 267.9 mmol). The yield of the acetylation product was 98% and the quality of PIB-acetate in the best fraction was 94.4 w/w % according to GC. Some PIB resulting from deacetylation during the distillation was detected in the distillation residue (up to 1.2 w/w %). Overall, the isolated yield from the 2 step process was 97%.

The invention claimed is:

1. A process for manufacturing a 3-unsubstituted, 3-monosubstituted or 3,3-disubstituted 9-acyloxy-1-5-dihydro-8-methylpyrido [3,4-e] [1,3]dioxepin of general formula

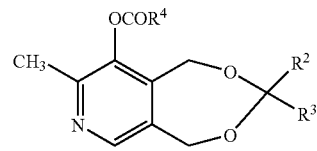

I wherein each of $R^2$ and $R^3$, independently, is hydrogen, $C_{1-4}$-alkyl, $C_{2-4}$-alkenyl, phenyl-$C_{1-4}$-alkyl or phenyl, or $R^2$ and $R^3$ together with the carbon atom to which they are attached signify $C_4$- to $C_6$-cycloalkylidene, and $R^4$ is $C_{1-4}$-alkyl or $C_{1-4}$-haloalkyl, and optionally for manufacturing pyridoxine, wherein the process comprises performing addition reaction between a 4-methyl-5-alkoxy-oxazole of the general formula

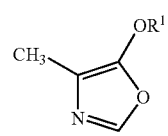

II wherein $R^1$ is $C_{1-4}$-alkyl, and a 2-unsubstituted, 2-monosubstituted or 2,2-disubstituted 4,7-dihydro-(1,3)-dioxepin of the general formula

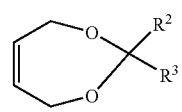

III wherein $R^2$ and $R^3$ are as defined above, in the substantial absence of a solvent and a catalyst to give a product mixture consisting essentially of the appropriate Diels-Alder adduct of the general formula

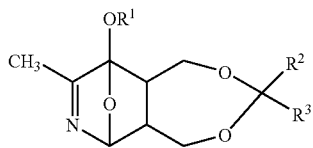

wherein R¹ and R² and R³ are as defined above,
in a major proportion and the appropriate 3-unsubstituted, 3-monosubstituted or 3,3-disubstituted 1,5-dihydro-8-methylpyrido[3,4-e] [1,3]dioxepin-9-ol of the general formula

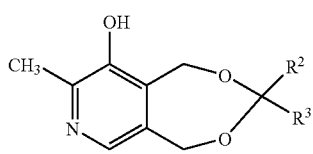

wherein R² and R³ are as defined above,
in a minor proportion,
removal of a substantial proportion of the unreacted starting materials of formulae II and III from the product mixture by distillation under reduced pressure,
addition of a substantially anhydrous organic acid to said product mixture and rearrangement of the Diels-Alder adduct of the formula IV present therein to further 3-unsubstituted, 3-monosubstituted or 3,3-disubstituted 1,5-dihydro-8-methylpyrido[3,4-e] [1,3]dioxepin-9-ol of the formula V in the presence of said substantially anhydrous organic acid with removal of the generated alkanol R¹OH by distillation under reduced pressure, and
acylation of the resultingly enriched quantity of the methylpyrido[3,4-e] [1,3]dioxepin-9-ol of the formula V with an added carboxylic acid anhydride of the general formula

    VI wherein R⁴ is as defined above,
to produce the desired 3-unsubstituted, 3-monosubstituted or 3,3-disubstituted 9-acyloxy-1,5-dihydro-8-methylpyrido[3,4-e] [1,3]dioxepin of the formula I,
and optionally converting this so-manufactured acylation product of the formula I to pyridoxine by acid hydrolysis for achieving deprotection and deacylation.

2. The process according to claim 1, wherein the starting materials of formulae II and III are 5-ethoxy-4-methyl-oxazole (formula II, wherein R¹ is ethyl) and 2-isopropyl-4,7-dihydro-(1,3)-dioxepin (formula III, wherein R² is hydrogen and R³ is isopropyl), respectively.

3. The process according to claim 1, wherein the process step involving the reaction of the starting materials of formulae II and III is effected at temperatures from about 130° C. to about 170° C., preferably from about 145° C. to about 160° C.

4. The process according to claim 1, wherein the molar ratio of the dihydrodioxepin of the formula III to the 4-methyl-5-alkoxy-oxazole of the formula II in the reaction mixture is from about 0.5:1 to about 5:1, preferably from about 1:1 to about 2:1.

5. The process according to claim 1, wherein distillation under reduced pressure for the removal of a substantial proportion of the unreacted starting materials of the formulae II and III from the product mixture obtained after the first step is effected by at a pressure in the range from about 10 mbar (1 kPa) to about 100 mbar (10 kPa).

6. The process according to claim 1, wherein an organic acid with a pKa value of up to about 5, preferably a $C_{2-5}$-alkanoic acid or a corresponding mono- or multihalogenated $C_{2-5}$-alkanoic acid, most preferably acetic acid, is used as the substantially anhydrous organic acid for the rearrangement of the Diels-Alder adduct of the formula IV to further 3-unsubstituted, 3-monosubstituted or 3,3-disubstituted 1,5-dihydro-8-methylpyrido[3,4-e] [1,3]dioxepin-9-ol of the formula V.

7. The process according to claim 1, wherein the amount of substantially anhydrous organic acid added for the rearrangement of the Diels-Alder adduct is from about 0.01 to about 2.0 equivalents per equivalent of said adduct.

8. The process according to claim 1, wherein the temperature of the product mixture to which the substantially anhydrous acid is added for the rearrangement of the Diels-Alder adduct is from about 50° C. to about 115° C.

9. The process according to claim 1, wherein the rearrangement of the Diels-Alder adduct with distillation of the generated alcohol R¹OH is effected at a reduced pressure from about 300 mbar (30 kPa) to about 700 mbar (70 kPa).

10. The process according to claim 1, wherein the carboxylic acid anhydride used for the acylation of the methylpyrido[3,4-e] [1,3]dioxepin-9-ol of the formula V corresponds to the anhydride of the substantially anhydrous acid used in the previous process step, and is preferably acetic anhydride.

11. The process according to claim 1, wherein the amount of carboxylic acid anhydride employed for the acylation is from about 1.05 to about 2 equivalents per equivalent of the methylpyrido[3,4-e] [1,3]dioxepin-9-ol to be acylated.

12. The process according to claim 1, wherein the temperature at which the acylation is effected is from about 50° C. to about 115° C.

13. The process according to claim 1, wherein the process is carried out continuously for two or more steps.

14. The process according to claim 1, wherein the optional final step of converting the so manufactured acylation product of the formula I to pyridoxine is realized by procedures well known in the prior art and, depending on the type of acid involved in the acid hydrolysis, produces pyridoxine in the form of the appropriate acid salt.

15. The process according to claim 14, wherein pyridoxine hydrochloride is produced.

16. The process according to claim 1, wherein distillation under reduced pressure for the removal of a substantial proportion of the unreacted starting materials of the formulae II and III from the product mixture obtained after the first step is effected by at a pressure in the range from about 20 mbar (2 kPa) to about 50 mbar (5 kPa).

17. The process according to claim 1, wherein distillation under reduced pressure for the removal of a substantial proportion of the unreacted starting materials of the formulae II and III from the product mixture obtained after the first step is effected by at a pressure in the range from about 35 mbar (3.5 kPa) to about 45 mbar (4.5 kPa).

18. The process according to claim 1, wherein the amount of substantially anhydrous organic acid added for the rearrangement of the Diels-Alder adduct is from about 1 to about 1.5 equivalents per equivalent of said adduct.

19. The process according to claim 1, wherein the temperature of the product mixture to which the substantially anhydrous acid is added for the rearrangement of the Diels-Alder adduct is from about 70° C. to about 90° C.

20. The process according to claim 1, wherein the amount of carboxylic acid anhydride employed for the acylation is from about 1.1 to about 1.5 equivalents per equivalent of the methylpyrido[3,4-e] [1,3]dioxepin-9-ol to be acylated.

21. The process according to claim 1, wherein the temperature at which the acylation is effected is from about 70° C. to about 90° C.

* * * * *